United States Patent
Shen et al.

(10) Patent No.: US 10,926,096 B2
(45) Date of Patent: Feb. 23, 2021

(54) METHOD FOR PROCESSING AND DISPLAYING INTRACAVITY ELECTROCARDIOGRAPHY SIGNAL AND TEMPORARY CARDIAC PACEMAKER WITH FUNCTION

(71) Applicant: LIFETECH SCIENTIFIC (SHENZHEN) CO., LTD, Shenzhen (CN)

(72) Inventors: Xiaonan Shen, Shenzhen (CN); Lepeng Zeng, Shenzhen (CN)

(73) Assignee: LIFETECH SCIENTIFIC (SHENZHEN) CO., LTD, Shenzhen (CN)

( * ) Notice: Subject to any disclaimer, the term of this patent is extended or adjusted under 35 U.S.C. 154(b) by 0 days.

(21) Appl. No.: 16/649,346

(22) PCT Filed: Sep. 17, 2018

(86) PCT No.: PCT/CN2018/105940
§ 371 (c)(1),
(2) Date: Mar. 20, 2020

(87) PCT Pub. No.: WO2019/057004
PCT Pub. Date: Mar. 28, 2019

(65) Prior Publication Data
US 2020/0297229 A1    Sep. 24, 2020

(30) Foreign Application Priority Data

Sep. 22, 2017   (CN) .......................... 201710868283.5

(51) Int. Cl.
*A61N 1/37*    (2006.01)
*A61B 5/04*    (2006.01)
(Continued)

(52) U.S. Cl.
CPC .......... *A61N 1/3706* (2013.01); *A61B 5/0402* (2013.01); *A61B 5/04012* (2013.01);
(Continued)

(58) Field of Classification Search
None
See application file for complete search history.

(56) References Cited

U.S. PATENT DOCUMENTS 4,601,291 A * 7/1986 Boute ................ A61N 1/37247
600/510
5,088,488 A * 2/1992 Markowitz ........ A61N 1/37211
600/519

(Continued)

FOREIGN PATENT DOCUMENTS

CN    104337510 A    2/2015
CN    104606784 A    5/2015
(Continued)

OTHER PUBLICATIONS

International Search Report dated Dec. 27, 2018 and Written Opinion in corresponding International application No. PCT/CN2018/105940; 10 pages.

(Continued)

*Primary Examiner* — Kennedy Schaetzle
(74) *Attorney, Agent, or Firm* — Maier & Maier, PLLC

(57) ABSTRACT

A temporary cardiac pacemaker including an acquisition module for acquiring an intracavity electrocardiography signal; a pre-processing module, connected to the acquisition module, for pre-processing the intracavity electrocardiography signal; a storage module, connected to the pre-processing module, for storing the pre-processed intracavity electrocardiography signal in real time; and a display control module, connected to the storage module, for display control. The display control module includes a display and an (Continued)

instruction determination unit for detecting whether a pacing parameter adjustment instruction is triggered and to call and display the intracavity electrocardiography signal stored in real time on a pacing parameter adjustment interface, which displays the intracavity electrocardiography signal stored in real time and the pacing adjustment parameter on the display; and the displayed information includes intracavity electrocardiography and electrocardiography event markers. The pre-processing module includes an electrocardiography event marking unit for performing electrocardiography event marking on the pre-processed intracavity electrocardiography signal.

5 Claims, 3 Drawing Sheets

(51) Int. Cl.
    *A61B 5/0402*     (2006.01)
    *A61B 5/00*     (2006.01)
    *A61N 1/362*     (2006.01)

(52) U.S. Cl.
    CPC ............ *A61B 5/7203* (2013.01); *A61N 1/362* (2013.01); *A61N 1/3704* (2013.01); *A61B 5/6852* (2013.01)

(56) References Cited

U.S. PATENT DOCUMENTS

| | | | |
|---|---|---|---|
| 5,522,857 A * | 6/1996 | van Krieken | A61N 1/365 607/14 |
| 5,549,654 A * | 8/1996 | Powell | A61N 1/37247 607/32 |
| 6,381,494 B1 * | 4/2002 | Gilkerson | A61N 1/37 607/27 |
| 6,434,424 B1 * | 8/2002 | Igel | A61N 1/3622 607/9 |
| 7,933,643 B1 * | 4/2011 | Gill | A61B 5/0402 600/510 |
| 10,575,740 B2 * | 3/2020 | Sanghera | A61B 5/0422 |
| 2002/0007198 A1 * | 1/2002 | Haupert | A61N 1/37235 607/30 |
| 2003/0045786 A1 * | 3/2003 | Zhao | G16H 50/50 600/372 |
| 2003/0135244 A1 * | 7/2003 | Esler | A61N 1/3706 607/27 |
| 2004/0106960 A1 * | 6/2004 | Siejko | A61N 1/3684 607/17 |
| 2007/0239230 A1 * | 10/2007 | Giftakis | A61B 5/4094 607/62 |
| 2008/0109041 A1 * | 5/2008 | de Voir | A61N 1/37 607/7 |
| 2008/0300497 A1 * | 12/2008 | Krause | A61B 5/0468 600/515 |
| 2008/0306390 A1 * | 12/2008 | Cinbis | A61N 1/3706 600/477 |
| 2011/0224988 A1 | 9/2011 | Mahajan et al. | |
| 2013/0289428 A1 * | 10/2013 | Patel | A61N 1/368 600/521 |
| 2015/0258341 A1 * | 9/2015 | Ternes | A61N 1/36142 607/17 |
| 2016/0121128 A1 * | 5/2016 | Fishler | A61N 1/37288 607/14 |
| 2016/0248434 A1 | 8/2016 | Govari | |

FOREIGN PATENT DOCUMENTS

| | | |
|---|---|---|
| CN | 104857633 A | 8/2015 |
| CN | 105148403 A | 12/2015 |
| CN | 106139401 A | 11/2016 |
| CN | 107693005 A | 2/2018 |
| WO | 2012128836 A1 | 9/2012 |

OTHER PUBLICATIONS

Chinese Office Action dated Jun. 3, 2019 in corresponding Chinese application No. 201710868283.5; 11 pages.
Notification to Grant Patent Right for Invention dated Feb. 26, 2020 in corresponding Chinese application No. 201710868283.5; 3 pages.

* cited by examiner

METHOD FOR PROCESSING AND DISPLAYING INTRACAVITY ELECTROCARDIOGRAPHY SIGNAL AND TEMPORARY CARDIAC PACEMAKER WITH FUNCTION

FIELD

The present application relates to the field of medical equipment, and more particularly relates to a method for processing and displaying an intracavity electrocardiography signal and a temporary cardiac pacemaker with this function.

BACKGROUND

Due to slow heart rate and arrhythmia, some patients suffer from impaired cardiac contractility, reduced pumping blood volume, insufficient blood perfusion in various organs of the body, and dysfunction caused by ischemia and hypoxia, and the heart may stop beating at any time, which endangers the lives of the patients. An emergency bedside temporary cardiac pacemaker may immediately increase the heart rate and improve ischemia and hypoxia, is the most effective and safest method for rescuing patients, and is the most direct method for increasing the heart rate of patients. The temporary cardiac pacemaker stimulates the myocardium by sending a pulse electric signal to cause excitation contraction of the heart, thereby replacing an original cardiac pacemaker and controlling the heart to contract according to a certain rhythm.

Intracavity electrocardiography signals are electric signals produced by the myocardial contraction and relaxation in a heart cavity, which show the activity of the heart. The intracavity electrocardiography signals with different features can indicate different pathological features of the heart and pacing capture. In general, intracavity electrocardiography signals may be acquired and combined with other parameters to indicate whether the output of a temporary cardiac pacemaker with a stimulating electrode inserted into the heart cavity successfully captures the heart, and indicate whether an electrode of an active pacing lead well predicts long-term implantation in long-term prognosis. However, the traditional temporary cardiac pacemaker only has a pacing output function, and an operator cannot timely check the current actual intracavity electrocardiography signal acquisition situation through the temporary cardiac pacemaker, and can only infer the pacing acquisition situation by observing a body surface electrocardiography signal through an external electrocardiograph monitor. Moreover, through the body surface electrocardiography signals provided by the external electrocardiograph monitor, it cannot be determined whether an electrode of an implanted pacing lead well predicts long-term implantation. The traditional temporary cardiac pacemaker must be operated and used by the aid of an external electrocardiograph monitor, a simple and convenient operation mode of simultaneously providing temporary pacing and observing intracavity electrocardiography signal functions by a single instrument is unavailable, the working efficiency is reduced, capture or not capture cannot be accurately indicated, and it cannot be indicated whether the implanted pacing lead well predicts long-term implantation, which greatly reduces the determination accuracy and real-time performance of the instrument.

Based on these, it is necessary to provide a temporary cardiac pacemaker which can intelligently display an intracavity electrocardiography signal according to actual needs, so as to improve the clinical determination accuracy and real-time performance of doctors and reduce the risk of misjudgment.

SUMMARY

Embodiments of the present application provide a method for processing and displaying an intracavity electrocardiography signal, which includes the following steps:

S1, acquiring an intracavity electrocardiography signal;

S2, pre-processing the intracavity electrocardiography signal;

S3, storing the pre-processed intracavity electrocardiography signal in real time;

S4, detecting whether a pacing parameter adjustment instruction is triggered, and if so, proceeding to the next step; and S5, invoking and displaying the intracavity electrocardiography signal stored in real time on a pacing parameter adjustment interface on the same screen.

In one embodiment, in step S2, pre-processing the intracavity electrocardiography signal includes: carrying out analog-to-digital conversion and noise filtering on the intracavity electrocardiography signal.

In one embodiment, in step S2, after pre-processing the intracavity electrocardiography signal, the method further includes: carrying out electrocardiography event marking on the pre-processed intracavity electrocardiography signal.

In one embodiment, in step S2, after carrying out electrocardiography event marking on the pre-processed intracavity electrocardiography signal, the method further includes: truncating an intracavity electrocardiography signal within a predetermined time range at a single electrocardiography event marker, storing the intracavity electrocardiography signal, and when it is detected that a pacing analysis instruction is triggered, invoking and displaying the truncated intracavity electrocardiography signal within the predetermined time range on a pacing analysis interface, on the same screen in real time.

In one embodiment, in step S2, after carrying out electrocardiography event marking on the pre-processed intracavity electrocardiography signal, the method further includes: converting a marker of an electrocardiography event into text information. Step S5 further includes: invoking and displaying the text information on the pacing parameter adjustment interface or the pacing analysis interface on the same screen in real time.

In one embodiment, the electrocardiography event includes at least one of a pacing event, a perception event, a refractory period perception event, and a noise event.

In one embodiment, in step S4, the pacing parameter adjustment instruction includes at least one of a frequency parameter adjustment instruction, a voltage parameter adjustment instruction, a pulse width parameter adjustment instruction, and a perception sensitivity adjustment instruction.

In one embodiment, the intracavity electrocardiography signal displayed in step S5 is a down-sampled signal.

The present application provides a temporary cardiac pacemaker, which includes: an acquisition module, configured to acquire an intracavity electrocardiography signal;

a pre-processing module, connected to the acquisition module, and configured to pre-process the intracavity electrocardiography signal;

a storage module, connected to the pre-processing module, and configured to store the pre-processed intracavity electrocardiography signal in real time; and a display control module, connected to the storage module, and configured for display control.

The display control module includes an instruction determination unit and a display, where the instruction determination unit is configured to detect whether a pacing parameter adjustment instruction is triggered, and the display is configured to call and display the intracavity electrocardiography signal stored in real time on a pacing parameter adjustment interface on the same screen.

The pre-processing module includes an analog-to-digital conversion unit for converting an analog signal into a digital signal and a filtering unit for filtering noise.

In one embodiment, the pre-processing module further includes an electrocardiography event marking unit for carrying out electrocardiography event marking on the pre-processed intracavity electrocardiography signal.

In one embodiment, a waveform alignment module between the pre-processing module and the storage module is further included. The waveform alignment module is configured to truncate an intracavity electrocardiography signal within a predetermined time range at a single electrocardiography event marker. When the instruction determination unit receives a pacing analysis instruction, the display displays the intracavity electrocardiography signal that is stored in the storage module and truncated by the waveform alignment module.

In one embodiment, a text module between the pre-processing module and the storage module is further included. The text module is configured to convert a marker of an electrocardiography event into text information. The display displays the text information while displaying the intracavity electrocardiography signal that is stored in the storage module.

In one embodiment, a sampling module between the pre-processing module and the storage module is further included. The sampling module is configured to down-sample the pre-processed electrocardiography signal.

The present application provides a method for processing and displaying an intracavity electrocardiography signal and a temporary cardiac pacemaker with this function. The temporary cardiac pacemaker acquires an intracavity electrocardiography signal and gives a corresponding display response according to a user selection, so that an operator can conveniently check the intracavity electrocardiography signal in time when needed, the working efficiency is improved, reference information is provided for operation and adjustment of subsequent parameters of the temporary cardiac pacemaker, and the operation accuracy is improved.

DETAILED DESCRIPTION OF THE EMBODIMENTS

In order that the embodiments may be better understood, the technical solutions of the present application will be described below with reference to various embodiments.

Figure 1:
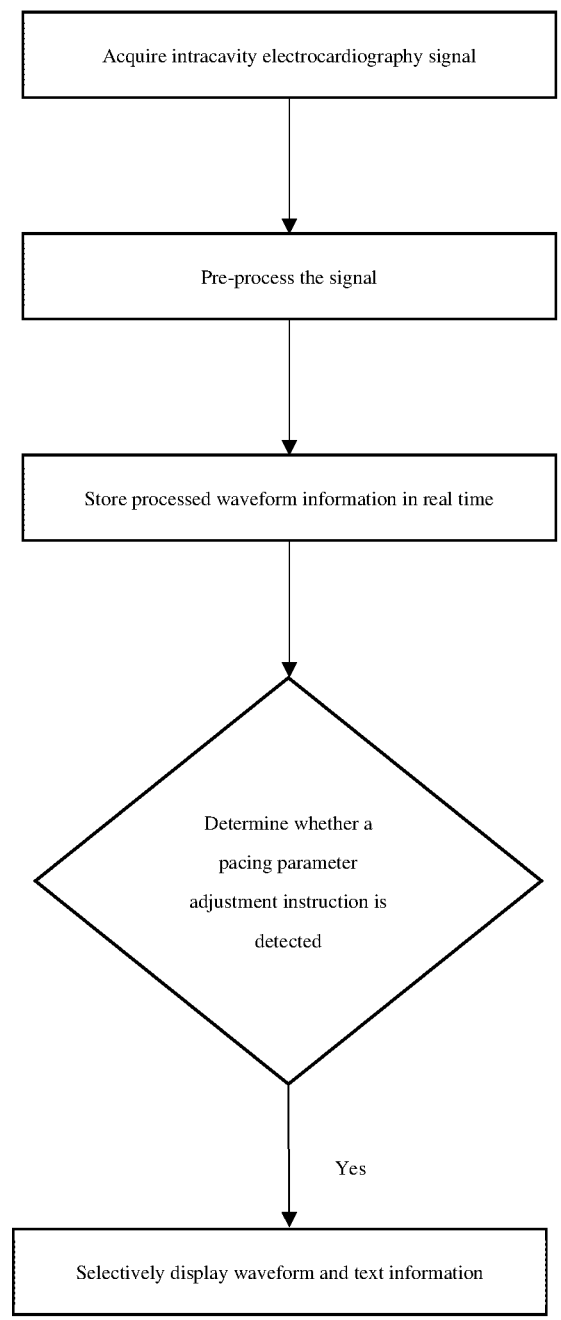
FIG. 1 is a flow chart of a method for processing and displaying an intracavity electrocardiography signal.

As shown in FIG. 1, a method for processing and displaying an intracavity electrocardiography signal according to the present application includes the following sequential steps that:

S1, acquiring an intracavity electrocardiography signal;

S2, pre-processing the intracavity electrocardiography signal;

S3, storing the pre-processed intracavity electrocardiography signal in real time;

S4, detecting whether a pacing parameter adjustment instruction is triggered, and if so, the next step is carried out; and S5, calling the intracavity electrocardiography signal stored in real time and displaying the intracavity electrocardiography signal on a pacing parameter adjustment interface on the same screen.

The intracavity electrocardiography signal acquired in step S1 is a voltage signal generated by a heart activity. The signal is a continuous analog signal, which is converted into a digital signal by pre-processing in step S2. The pre-processing step may include hardware band-pass filtering, analog-to-digital conversion and digital filtering. Only the pre-processed denoised signals within a frequency range of the heart activity are kept.

In step S2, after the pre-processing, the method may also include electrocardiography event marking processing, and algorithm processing such as signal noise extraction, signal peak searching and refractory period perception searching. Then, pacing event marking, perception event marking, refractory period perception event marking or noise event marking is carried out on the electrocardiography signal in the form of digital signal insertion according to the result. Of course, the marked electrocardiography event may be one or a combination of the above. For example, the electrocardiography event is marked according to the following logics: when a preset basic frequency times out, the electrocardiography event is marked as a pacing event; a signal peak value is searched within a certain time window according to a preset perception sensitivity when the electrocardiography signal exceeds a set value, and the electrocardiography event is marked as a perception event when a noise-to-signal peak ratio is smaller than a specific value such as 0.75; refractory period perception search is started, whether a perception event exists is searched within a certain window time, the electrocardiography event is marked as a refractory period perception event if the perception event still exists, and refractory period perception search is started until the preset basic pacing frequency times out; and after the refractory period search window period ends, noise detection is started, the searched noise is subjected to envelope processing to obtain a processed noise value, and the electrocardiography event is marked as a noise event when the noise value is greater than the perception sensitivity. A series of digital signals are obtained after marking, when the electrocardiography event is marked, specific numbers may be inserted into specific positions of the original digital signals. For example, the upper four bits of each byte in the digital signals may be specified to respectively represent a perception event bit, a pacing event bit, a refractory period perception event bit, and a noise event bit, and a corresponding bit value of '1' is represented as that electrocardiography event. In other embodiments, marking of noise events may not be carried out.

When step S2 is carried out, a step of truncating the intracavity electrocardiography signal within a predetermined time range before and after a single electrocardiography event marker in the intracavity electrocardiography signals subjected to electrocardiography event marking may be further included. For example, an intracavity electrocardiography digital signal which is subjected to electrocardiography event marking processing and contains electrocardiography event insertion information is read, a time axis corresponding to a waveform containing the electrocardiography event is marked, and by taking the marker as a starting point, an electrocardiography signal within a certain time range is truncated. For example, electrocardiography signals within the range of 100 milliseconds before and 300 milliseconds after the marking point can be truncated.

When step S2 is carried out, a step of converting the intracavity electrocardiography signal marked by the electrocardiography event marker into text information may also be included. For example, a pacing event, a perception event, a refractory period perception event, and a noise event are denoted by P, S, R, and N, respectively.

In other embodiments, the textual information may be other graphics or symbols that distinguish electrocardiography events.

In step S3, the signal processed in step S2 is stored in real time. Meanwhile, it is also possible to separately store the signals subjected to various processes in step S2, for example, to separately store analog-to-digital converted and filtered signals, truncated signals within a certain time range, text information, etc. into different buffer units.

In steps S4 and S5, it is detected whether there is a specific external instruction, if there is a pacing parameter adjustment instruction, the pre-processed electrocardiography signal stored in step S3 is displayed on a pacing parameter adjustment interface, and after the instruction is triggered, the interface displays real-time continuous waveform signals in addition to parameter information. The foregoing pacing parameter adjustment instruction is one or more conventional adjustment instructions regarding pacing signal frequency, voltage, pulse width and perception sensitivity as recognized by a person skilled in the art, i.e., a frequency parameter adjustment instruction, a voltage parameter adjustment instruction, a pulse width parameter adjustment instruction, and a perception sensitivity adjustment instruction. Correspondingly, the pacing parameter adjustment interface may display corresponding pacing parameters. For example, after receiving the frequency parameter adjustment instruction, the pacing parameter adjustment interface may display the current pacing frequency information in addition to the intracavity electrocardiography signal waveform. Further, if the pacing analysis instruction is detected in step S4, the intracavity electrocardiography signal truncated within a certain time range and stored in step S3 is transferred and displayed on a pacing analysis interface, and the pacing analysis interface correspondingly displays the truncated intracavity electrocardiography signal and simultaneously displays partial feature values of the current signal.

In some embodiments, text information representing an electrocardiography event may also be displayed on the same screen, with the text information corresponding to a waveform signal of an electrocardiography event, and further, the text information may be displayed in rows to avoid text overlap. For example, a pacing event may be generated immediately after a refractory period perception event or a noise event occurs, for avoiding text overlapping, when the pacing event is displayed, the text representing the pacing event occupies one line independently, and other events are displayed on the other line, so that an operator can view the pacing event more conveniently, unnecessary trouble for subsequent operation and determination due to no timely and clear display caused by the simultaneous occurrence of special events is avoided, and the operation accuracy is reduced.

In some other embodiments, the pacing parameter adjustment interface may simultaneously display a perception sensitivity horizontal line when a perception sensitivity adjustment instruction is received, and the distance of the horizontal line from an intracavity electrocardiography signal level baseline is the currently set perception sensitivity. The displayed perception sensitivity horizontal line indicates the current perception sensitivity and is directly compared with the displayed waveform signal, and an operator may directly adjust the perception sensitivity according to the comparison. When the perception sensitivity is adjusted, the horizontal line may move up and down, the change of the perception sensitivity along with the adjustment is reflected in real time, i.e., when the perception sensitivity value is adjusted to be high, the horizontal line moves to the direction far away from the baseline, and when the perception sensitivity value is adjusted to be low, the horizontal line moves to the direction close to the baseline. In this way, the operator may make quick adjustment while quickly determining whether the current sensitivity is suitable through the relative position of the horizontal line of the perception sensitivity and an electrocardiography signal waveform peak value. Compared with the traditional practice, the operator cannot view a waveform diagram, needs to set a lower sensitivity value and then slowly adjust and try, finally obtains a suitable perception sensitivity value by experience, which may also be influenced by a noise signal. The display mode may quickly and accurately help the operator to adjust the perception sensitivity.

In some other embodiments, perception sensitivity horizontal lines may also be provided both above and below the electrocardiography signal level baseline, the two horizontal lines being equidistant from the baseline and both near or far from the baseline simultaneously as the sensitivity is adjusted by the operator.

In order to display more signal waveforms within the same time range after triggering the pacing parameter adjustment instruction, the signal may be subjected to analog-to-digital conversion and filtering in step S2 and then down-sampled, for example, sampled in a ratio of 4:1 after waveform feature values of the signal is extracted.

Figure 2:
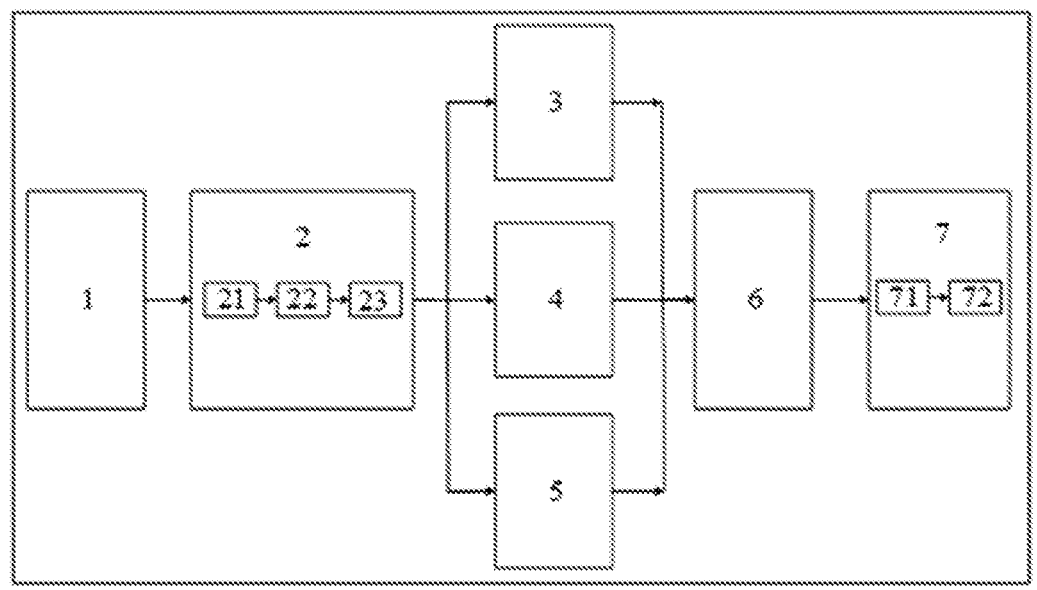
FIG. 2 is a schematic structural diagram of a temporary cardiac pacemaker with a function of processing and displaying an intracavity electrocardiography signal.

As shown in FIG. 2, a temporary cardiac pacemaker with a function of processing and displaying an intracavity electrocardiography signal according to the present application is in contact with a cardiac chamber through a pacing lead and includes an acquisition module 1, a pre-processing module 2, a sampling module 3, a waveform alignment module 4, a text module 5, a storage module 6, and a display control module 7. The acquisition module 1 acquires an intracavity electrocardiography signal through the pacing lead; the pre-processing module 2 is connected to the acquisition module 1; the sampling module 3, the waveform alignment module 4 and the text module 5 are in parallel relation, are connected to the pre-processing module 2, and simultaneously receive an information flow from the pre-processing module 2; the storage module 6 is respectively connected to the sampling module 3, the waveform alignment module 4 and the text module 5 through an SPI interface; and the display control module 7 is connected to the storage module 6. The pre-processing module 2, the sampling module 3, the waveform alignment module 4 and the text module 5 are all functional parts in a first microprocessor with an SPI master-slave interface, an external interrupt GPIO, a general GPIO, a RAM, and a ROM. The information transmission among the above functional modules is realized through the SPI interface.

The acquisition module 1 is configured to acquire an intracavity electrocardiography signal; the pre-processing module 2 pre-processes the acquired intracavity electrocardiography signal, where the pre-processing may include analog-to-digital conversion and noise filtering processing, and may further include electrocardiography event marking processing on the electrocardiography signal; the sampling module 3 compresses and samples the pre-processed electrocardiography signal; in addition, the waveform alignment module 4 truncates a signal marked by an electrocardiography event and keeps the signal within a certain time range when a single electrocardiography event occurs; meanwhile, the text module 5 reads the signal marked by the electrocardiography event and converts electrocardiography event information into text information; the storage module 6 stores the information transmitted by the foregoing modules; and according to an external instruction, the display control module 7 may switch a display picture, that is, selectively display the sampled electrocardiography signal or the truncated electrocardiography signal within a certain time range, and simultaneously display the text information.

In some other embodiments, one or more of the sampling module 3, the waveform alignment module 4 and the text module 5 may also be selectively omitted.

For example, the acquisition module 1 acquires an intracavity electrocardiography signal through a pacing lead and transmits the acquired signal to the pre-processing module 2, and the module includes an analog-to-digital conversion unit 21 and a filtering unit 22. The analog-to-digital conversion unit 21 converts an acquired analog signal into a digital signal which is more favorable for digital processing, and may be a high-precision ADC chip. The filtering unit 22 is configured to filter out signals outside a target frequency band. For example, in the present embodiment, it is necessary to filter out signals outside of a frequency range of 1-65 Hz while retaining heart activity electrical signals, so that the filtering unit 22 may be configured to include two first-order digital low-pass filters, three first-order high-pass filters, a digital trap of 50 Hz, a digital trap of 60 Hz, a digital trap of 100 Hz, a digital trap of 120 Hz, and a digital rectifier, which are connected in sequence. Further, the pre-processing module 2 may further include an electrocardiography event marking unit 23. The electrocardiography event marking unit 23 performs electrocardiography event marking on the digital signal by a series of algorithms, for example, performs electrocardiography event marking on the electrocardiography signal processed by the filtering unit 22 by algorithms such as noise extraction, signal peak search and refractory period perception search to obtain a series of digital signals. When the digital signal is marked, marking may be carried out by inserting a specific number at a specific position of the digital signal. For example, the upper four bits of the digital signal may be respectively specified as a perception event bit, a pacing event bit, a refractory period perception event bit, and a noise event bit, and a corresponding bit value of '1' is represented as the electrocardiography event.

The electrocardiography event marking unit 23 marks the electrocardiography event according to the following logics: when a preset basic frequency times out, the electrocardiography event is marked as a pacing event; a signal peak value is searched within a certain time window according to a perception sensitivity set by a user when the electrocardiography signal exceeds a set value, and then the electrocardiography event is marked as a perception event when a noise-to-signal peak ratio is smaller than a certain value such as 0.75; then refractory period perception search is started to search whether a perception event exists within a certain window time, the electrocardiography event is marked as a refractory period perception event if the perception event still exists, and refractory period perception search is started until the basic pacing frequency set by the user times out; and after the refractory period search window period ends, starting to detect noise, the searched noise is subjected to envelope processing to obtain a processed noise value, and the electrocardiography event is marked as a noise event when the noise value is greater than the perception sensitivity.

In other embodiments, the marking unit 23 may also mark only a perception event and a pacing event.

In other embodiments, a series of hardware filters may also be included before the analog-to-digital conversion unit 21, such as a multi-stage hardware band-pass filter for filtering high frequency noise in the environment and low frequency noise introduced by the patient's breathing.

The sampling module 3 receives the intracavity electrocardiography signal processed by the pre-processing module 2, groups the received signals in a digital form, extracts feature value information such as a maximum value, a minimum value and a slope of grouped data, samples the feature values in a certain ratio, for example, in a ratio of 4:1 adopted in the present embodiment, to form waveform image data. The waveform images are continuous waveforms, the waveforms of a plurality of electrocardiography events may be displayed on the display due to sampling processing, and it can be intuitively determined whether the output of the temporary cardiac pacemaker successfully captures the heart.

After the waveform alignment module 4 receives the signal marked by the electrocardiography event marking unit 23 in the storage module 2, a time axis corresponding to a waveform containing the electrocardiography event is marked, and by taking the marker as a starting point, an electrocardiography signal within a certain time range is truncated. For example, electrocardiography signals within the range of 100 milliseconds before and 300 milliseconds after the marking point can be truncated. Because the electrocardiography signal only truncates the waveform generated when the electrocardiography signal event occurs, most of the electrocardiography signal waveforms generated when no electrocardiography signal event occurs are abandoned, so that the waveform contains more detailed information, the damage current condition may be displayed in detail, and the implantation condition of an implantation lead of an active pacemaker can be determined.

After receiving the signal marked by the electrocardiography event marking unit 23 in the storage module 2, the text module 5 converts the digital information into text character string information. For example, a pacing event, a perception event, a refractory period perception event, and a noise event are denoted by P, S, R, and N, respectively.

In other embodiments, the textual information may be other graphics or symbols that distinguish electrocardiography events.

The storage module 6 stores the information further processed by the pre-processing module 2, the sampling module 3, the waveform alignment module 4 and the text information module 5 for the subsequent display of the display control module. In other embodiments, the storage module 6 may be a memory unit disposed within the pre-processing module 2, the sampling module 3, the waveform alignment module 4, and the text information module 5, respectively.

Figure 3:
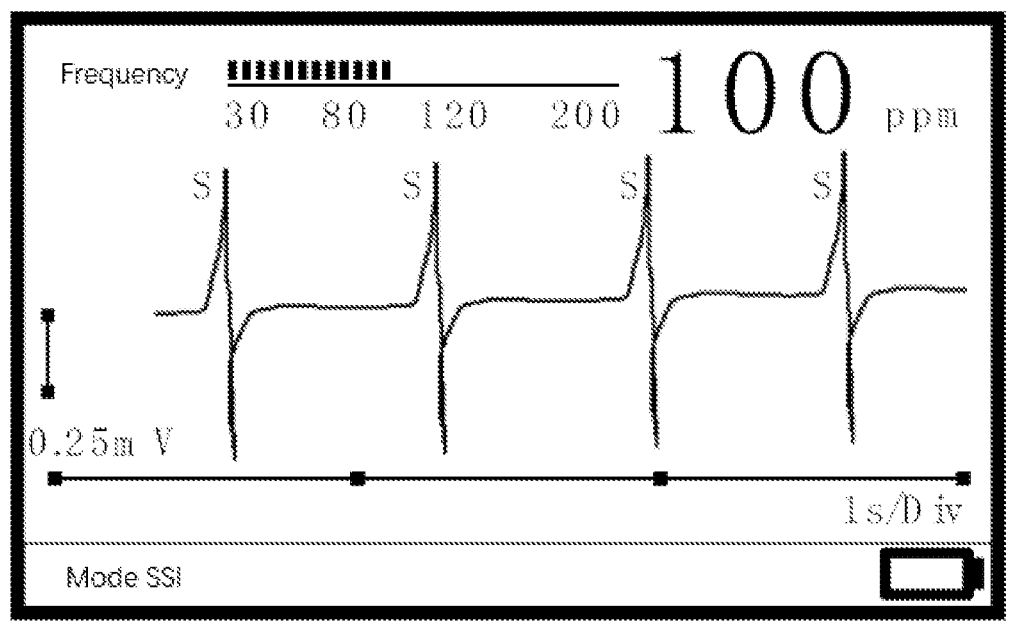
FIG. 3 is a schematic diagram of a display mode of a temporary cardiac pacemaker with a function of processing and displaying an intracavity electrocardiography signal.
Figure 4:
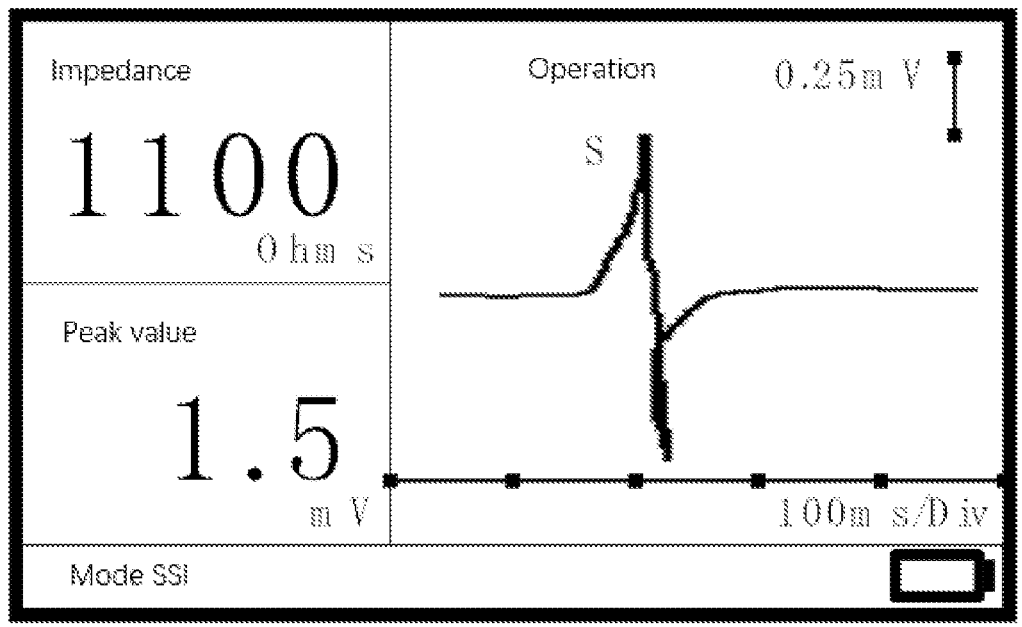
FIG. 4 is a schematic diagram of another display mode of a temporary cardiac pacemaker with a function of processing and displaying an intracavity electrocardiography signal.

The display control module 7 includes an instruction determination unit 71 and a display 72. The instruction determination unit 71 determines an externally input instruction, responds to the instruction, and calls corresponding information in the storage module 6 to be displayed on the display 72. When the instruction determination unit 71 receives the pacing parameter adjustment instruction, a waveform signal stored in the storage unit 6 is called and displayed, and as previously described, this partially displayed waveform may be a continuous waveform signal down-sampled by the sampling module 3, or an unsampled signal, preferably a sampled signal, as shown in FIG. 3. In this way, the intracavity electrocardiography signal is specifically displayed and called for a special instruction, waveforms containing a large number of electrocardiography events may be displayed, an operator can conveniently check the intracavity electrocardiography signal in time when needed, the working efficiency is improved, reference information is provided for operation and adjustment of subsequent parameters of the intracavity electrocardiography signal, and the operation accuracy is improved. If the instruction determination unit 71 receives the pacing analysis instruction, the waveform signal stored in the storage unit 6 and truncated by the waveform alignment module 4 is called and displayed, as shown in FIG. 4. In this way, an injury current may be reflected on the intracavity electrocardiography signal, the detailed waveform information of an electrocardiography event can be observed, information on the waveform change caused by the injury current can be carefully observed, the implantation condition of a pacing lead may be reflected, and a powerful reference is provided for the follow-up operation of an operator. The pacing parameter adjustment instruction includes a frequency parameter adjustment instruction, a voltage parameter adjustment instruction, a pulse width parameter adjustment instruction, and a perception sensitivity adjustment instruction, and the display 72 refreshes and displays the electrocardiography waveform signal in real time.

On the pacing parameter adjustment interface, the intracavity electrocardiography signal stored in real time and the pacing adjustment parameter are displayed up and down side by side on the same screen. For example, in the frequency parameter adjustment interface in FIG. 3, the frequency adjustment range and the currently adjusted frequency value are displayed above the display screen, and meanwhile, the intracavity electrocardiography signal stored in real time is vertically side by side and preferably displayed below the screen, which facilitates the viewing of more complete waveform information.

In some embodiments, text information representing an electrocardiography event may also be displayed on the same screen, with the text information corresponding to a waveform signal of an electrocardiography event, and further, the text information may be displayed in rows to avoid text overlap. For example, a pacing event may occur immediately after a refractory period perception event or a noise event occurs, text overlap is avoided, when the pacing event is displayed, the text representing the pacing event occupies one line independently, and other events are displayed on the other line.

Figure 5:
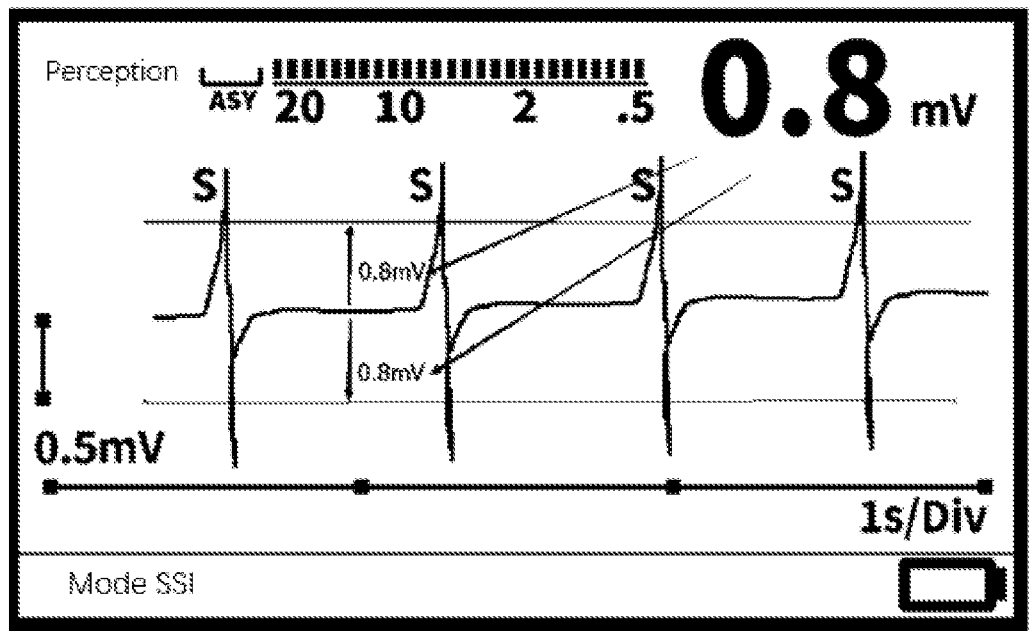
FIG. 5 is a schematic diagram of a display mode of a temporary cardiac pacemaker with a function of processing and displaying an intracavity electrocardiography signal in one embodiment.

As shown in FIG. 5, in some other embodiments, the display 72 may simultaneously display a perception sensitivity horizontal line on the pacing parameter adjustment interface when receiving a perception sensitivity adjustment instruction, and the distance of the horizontal line from an electrocardiography signal level baseline is the currently set perception sensitivity. The displayed perception sensitivity horizontal line indicates the current perception sensitivity and is directly compared with the displayed waveform signal, and an operator may directly adjust the perception sensitivity according to the comparison. When the perception sensitivity is adjusted, the horizontal line may move up and down, the change of the perception sensitivity along with the adjustment is reflected in real time, i.e., when the perception sensitivity value is adjusted to be high, the horizontal line moves to the direction far away from the baseline, and when the perception sensitivity value is adjusted to be low, the horizontal line moves to the direction close to the baseline. In this way, the operator may make quick adjustment while quickly determining whether the current sensitivity is suitable through the relative position of the horizontal line of the perception sensitivity and an electrocardiography signal waveform peak value.

In other embodiments, perception sensitivity horizontal lines may also be provided both above and below the electrocardiography signal level baseline, the two horizontal lines being equidistant from the baseline and both near or far from the baseline simultaneously as the sensitivity is adjusted by the operator.

In other embodiments, a scale may be displayed on a longitudinal axis of the electrocardiography signal waveform so as to quickly read the current waveform peak value and the perception sensitivity value for convenience of quick adjustment. The scale may be preferably disposed on both sides of the screen, the longitudinal axis is an amplitude scale, and the calibration does not start from a zero point, thereby saving the display space, and increasing the display area of an intracavity electrocardiogram. The scale facilitates checking and amplitude determination. The amplitude scale may be preset. As another preferred mode, because the intracavity electrocardiogram is influenced by various factors according to the size of a detected signal, the amplitude values are not fixed, and may vary with each user, device or pacing lead, the system may automatically detect the amplitude range displayed by the current intracavity electrocardiogram and carry out self-adaptive scale adjustment, so that the effect that an operator checks more conveniently and the subsequent operation accuracy is guaranteed is achieved.

In other embodiments, a horizontal axis scale may also be displayed below or above the electrocardiography signal waveform, the scale unit may be set to 1 lattice per second, and the operator may quickly approximate the interval of the perception event or the pacing event, infer the heart rate of a patient, and quickly set reasonable pacing parameters.

In summary, when the temporary cardiac pacemaker according to the present application is used, the acquisition module 1 acquires an electrocardiography signal in a heart cavity of a patient through a pacing lead, may also acquire a signal from other signal sources and transmit the signal to the pre-processing module 2 for processing, and may perform various processing such as analog-to-digital conversion, filtering, electrocardiography event marking, signal sampling, signal truncating, text conversion and the like; the storage module 6 receives and stores the processed signal; and the instruction determination unit 71 pays attention to an external instruction at any time, invokes the signal stored in the storage module 6 to be displayed on the display 72 when an instruction which may trigger waveform display is detected, and may switch display pictures according to different instructions.

The foregoing detailed description is merely illustrative of the technical solution of the present application rather than limiting the present application. Persons of ordinary skill in the art can make changes to corresponding units or parameters according to actual requirements. For example, the signal pre-processing unit may adopt different numbers of digital filters according to requirements. In the design including the waveform alignment module, waveform signals within other time ranges may also be truncated. In the design including the sampling module, a sampling ratio may also be changed. It should be noted that a system of the temporary cardiac pacemaker according to the present application for displaying an intracavity electrocardiography signal may also be used with other instruments or devices that require display of the intracavity electrocardiography signal, not limited to the temporary cardiac pacemaker.

The invention claimed is:

1. A temporary cardiac pacemaker, comprising:
an acquisition module, configured to acquire an intracavity electrocardiography signal;
a pre-processing module, connected to the acquisition module, and configured to pre-process the intracavity electrocardiography signal;
a storage module, connected to the pre-processing module, and configured to store the pre-processed intracavity electrocardiography signal in real time; and
a display control module, connected to the storage module, and configured for display control,
wherein the display control module comprises an instruction determination unit and a display, the instruction determination unit is configured to detect whether a pacing parameter adjustment instruction is triggered, and the instruction determination unit is configured to call and display the intracavity electrocardiography signal stored in real time on a pacing parameter adjustment interface, the pacing adjustment interface displaying the intracavity electrocardiography signal stored in real time and the pacing adjustment parameter on the display; and the displayed information includes intracavity electrocardiography and electrocardiography event markers; and
wherein the pre-processing module further comprises an electrocardiography event marking unit for carrying out electrocardiography event marking on the pre-processed intracavity electrocardiography signal, and the electrocardiography event is marked according to the following logics: when a preset basic frequency times out, the electrocardiography event is marked as a pacing event; a signal peak value is searched within a certain time window according to a preset perception sensitivity when the electrocardiography signal exceeds a set value, and the electrocardiography event is determined marked as a perception event when a noise-to-signal peak ratio is smaller than a specific value; refractory period perception search is started, whether a perception event exists is searched within a certain window time, the electrocardiography event is marked as a refractory period perception event if the perception event still exists, and refractory period perception search is started until the preset basic pacing frequency times out; and after the refractory period search window period ends, noise detection is started, the searched noise is subjected to envelope processing to obtain a processed noise value, and the electrocardiography event is marked as a noise event when the noise value is greater than the perception sensitivity, and the marked electrocardiography event may be one or a combination of the above.

2. The temporary cardiac pacemaker according to claim 1, wherein the pre-processing module comprises an analog-to-digital conversion unit for converting an analog signal into a digital signal and a filtering unit for filtering noise.

3. The temporary cardiac pacemaker according to claim 1, further comprising a waveform alignment module between the pre-processing module and the storage module, wherein the waveform alignment module is configured to truncate an intracavity electrocardiography signal within a predetermined time range at a single electrocardiography event marker, and when the instruction determination unit receives a pacing analysis instruction, the display displays the intracavity electrocardiography signal that is stored in the storage module and truncated by the waveform alignment module.

4. The temporary cardiac pacemaker according to claim 1, further comprising a text module between the pre-processing module and the storage module, wherein the text module is configured to convert a marker of an electrocardiography event into text information, and the display displays the text information while displaying the intracavity electrocardiography signal that is stored in the storage module.

5. The temporary cardiac pacemaker according to claim 1, further comprising a sampling module between the pre-processing module and the storage module, wherein the sampling module is configured to down-sample the pre-processed electrocardiography signal.

* * * * *